United States Patent
Böehm et al.

[11] Patent Number: 6,136,976
[45] Date of Patent: Oct. 24, 2000

[54] PROCESS FOR PRODUCING PERYLENE-3, 4-DICARBOXYLIC ACID IMIDES

[75] Inventors: Arno Böehm, Mannheim; Harald Arms, Worms; Willi Helfer, Friedelsheim; Georg Henning, Ludwigshafen, all of Germany

[73] Assignee: BASF Aktiengesellschaft, Ludwigshafen, Germany

[21] Appl. No.: 09/147,353

[22] PCT Filed: May 28, 1997

[86] PCT No.: PCT/EP97/02761

§ 371 Date: Dec. 7, 1998

§ 102(e) Date: Dec. 7, 1998

[87] PCT Pub. No.: WO97/46533

PCT Pub. Date: Dec. 11, 1997

[30] Foreign Application Priority Data

Jun. 5, 1996 [DE] Germany .......... 196 22 673

[51] Int. Cl.[7] .......... C07D 471/00; C07D 401/12; C07D 403/12; C07D 239/28

[52] U.S. Cl. .......... 544/314; 544/318; 544/319; 546/39

[58] Field of Search .......... 546/39; 544/314, 544/318, 319

[56] References Cited

U.S. PATENT DOCUMENTS

| | | | |
|---|---|---|---|
| 5,405,962 | 4/1995 | Mullen et al. | 546/27 |
| 5,650,513 | 7/1997 | Langhals et al. | 546/38 |
| 5,808,073 | 9/1998 | Bohm et al. | 546/39 |
| 5,981,773 | 11/1999 | Langhals et al. | 549/381 |
| 5,986,099 | 11/1999 | Mullen et al. | 546/26 |

*Primary Examiner*—Alan L. Rotman
*Attorney, Agent, or Firm*—Oblon, Spivak, McClelland, Maier & Neustadt, P.C.

[57] ABSTRACT

Perylene-3,4-dicarboximides I

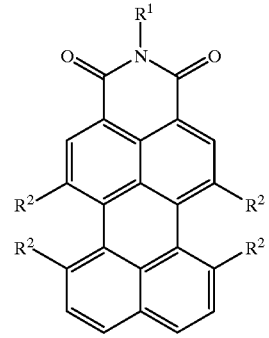

($R^1$ is hydrogen; $C_1$–$C_8$-alkyl; $C_5$–$C_8$-cycloalkyl; substituted or unsubstituted phenyl or naphthyl;

$R^2$ independently at each occurrence is hydrogen; $C_1$–$C_{18}$-alkyl, substituted or unsubstituted aryloxy, arylthio, hetaryloxy or hetarylthio)
are prepared by reacting the corresponding perylene-3,4,9,10-tetracarboxylic acid or its anhydride (II) with an amide III $$R^3\text{—CO—NHR}^1 \qquad \text{III}$$

($R^3$: $C_1$–$C_4$-alkyl or —$NR^4R^5$ where $R^4$ and $R^5$ independently are hydrogen or one of the $R^1$ alkyls, cycloalkyls, phenyls or naphthyls and where if two or more of $R^1$, $R^4$ and $R^5$ are other than hydrogen they are identical)
under superatmospheric pressure in the presence of an inert diluent and a transition metal catalyst.

7 Claims, No Drawings

PROCESS FOR PRODUCING PERYLENE-3, 4-DICARBOXYLIC ACID IMIDES

The present invention relates to a novel process for preparing perylene-3,4-dicarboximides of the formula I

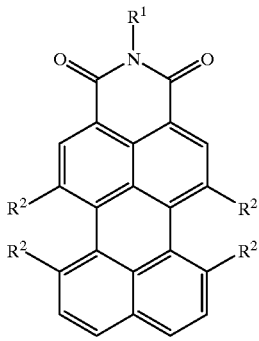

I where

R$^1$ is hydrogen; C$_1$–C$_8$-alkyl; C$_5$–C$_8$-cycloalkyl; or phenyl or naphthyl, each of which can be substituted by C$_1$–C$_{10}$-alkyl, C$_1$–C$_6$-alkoxy or cyano; and R$^2$ independently at each occurrence is hydrogen; C$_1$–C$_{18}$-alkyl; or aryloxy, arylthio, hetaryloxy or hetarylthio, each of which can be substituted by C$_1$–C$_{10}$-alkyl, C$_1$–C$_6$-alkoxy or cyano.

Perylene-3,4-dicarboximides of the formula I are known to be important intermediates in preparing pigment additives, fluorescent dyes and fluorescent pigments (EP-A-636 666; EP-A-596 292), but are also suitable themselves with advantage as fluorescent dyes and pigments (EP-A-657 436; nonprior-published DE-A-195 01 737).

To prepare perylene-3,4-dicarboximides I whose perylene framework is unsubstituted (R$^2$=H) a range of complex multistage processes have been described which start from perylene-3,4,9,10-tetracarboxylic dianhydride and which yield the compounds I in usually unsatisfactory yields and in such poor purity that complex purification methods, such as extraction and column chromatography, are required.

For instance, unsubstituted and N-alkyl-substituted perylene-3,4-dicarboximides (where alkyl is methyl, ethyl, n-propyl, n-butyl, isobutyl, n-pentyl, n-hexyl, n-octyl or n-dodecyl) are obtained by alkaline decarboxylation of the perylene-3,4,9,10-tetracarboxylic imide anhydride intermediates at ≧220° C. under superatmospheric pressure in reaction times of 18 h (DE-C-486 491; Bull. Chem. Soc. Jap. 54 (1981) 1575–1576; EP-A-596 292). This process, however, is suitable only for base-stable aliphatic imides.

To prepare the N-methyl- and N-ethyl- (and also N-phenyl-, N-tolyl- and N-anisyl-)substituted perylene-3,4-dicarboximides, the initially prepared unsubstituted perylene-3,4-dicarboximide is sulfonated with oleum and then converted with potassium hydroxide solution into the sulfonated anhydride, which is then reacted with the appropriate primary amine to form the sulfonated N-substituted imide, which finally is desulfonated using sulfuric acid to give the desired perylene-3,4-dicarboximide (Bull. Chem. Soc. Jap. 52 (1979) 1723–1726, Shikizai Kyokaishi 49 (1976) 29–34 = Chemical Abstracts 85:209285). This process is extremely laborious and can only be used for sulfuric-acid-stable imides.

In EP-A-657 436, unsubstituted, N-alkyl-, N-cycloalkyl- and N-phenyl-substituted perylene-3,4-dicarboximides with an unsubstituted perylene framework are obtained by condensing perylene-3,4,9,10-tetracarboxylic dianhydride with 2,5-di-tert-butylaniline in the presence of water, zinc acetate dihydrate and imidazol, by alkaline hydrolysis of the chromatographically purified N-2,5-di-tert-butylphenylperylenedicarboximide, to give the perylene-3,4-dicarboxylic anhydride, which is then reacted with the appropriate primary amine.

Another process described in EP-A-657 436 for preparing N-alkyl-substituted perylene-3,4-dicarboximides starts from the unsubstituted perylene-3,4-dicarboximide, which initially, as described above, can be prepared from perylene-3,4,9,10-tetracarboxylic dianhydride and is reacted with the appropriate alkyl bromide in the presence of a strong base and of a dipolar-aprotic solvent. In this case too the reaction products are chromatographed.

Finally, N-1-hexylheptyl- and N-1-octylnonyl-perylene-3,4-dicarboximide can in accordance with EP-A-657 436 also be obtained, by analogy with the N-2,5-di-tert-butylphenylperylene-3,4-dicarboximide intermediate, directly from perylene-3,4,9,10-tetracarboxylic dianhydride.

However, the preparation processes known from EP-A-657 436 as well are highly complex and produce only low overall yields of the N-substituted perylene-3,4-dicarboximides.

A process which is suitable inter alia for preparing perylene-3,4-dicarboximides which are substituted in the perylene framework is described in nonprior-published DE-A-195 01 737. Here, the imides I are obtained by direct reaction of perylene-3,4,9,10-tetracarboxylic dianhydride and primary amine in the presence of a tertiary nitrogen-basic compound, such as quinoline, and of zinc, copper or salts thereof as catalyst, without the addition of water.

It is the object of the present invention to provide a simple and economic process which is unhampered by the above disadvantages and which permits the preparation of perylene-3,4-dicarboximides, which may be substituted on the imide nitrogen and/or in the perylene framework, in good yields and in purities sufficient for the subsequent intended use.

We have found that this object is achieved by a process for preparing perylene-3,4-dicarboximides of the formula I

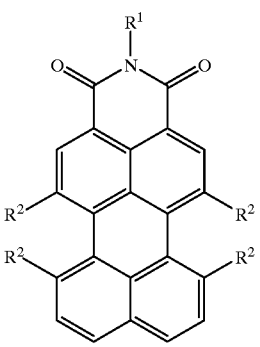

I where

R$^1$ is hydrogen; C$_1$–C$_8$-alkyl; C$_5$–C$_8$-cycloalkyl; or phenyl or naphthyl, each of which can be substituted by C$_1$–C$_{10}$-alkyl, C$_1$–C$_6$-alkoxy or cyano; and R$^2$ independently at each occurrence is hydrogen; C$_1$–C$_{18}$-alkyl; or aryloxy, arylthio, hetaryloxy or hetarylthio, each of which can be substituted by C$_1$–C$_{10}$-alkyl, C$_1$–C$_6$-alkoxy or cyano, which comprises reacting a perylene-3,4,9,10-tetracarboxylic acid or its anhydride of the formula II

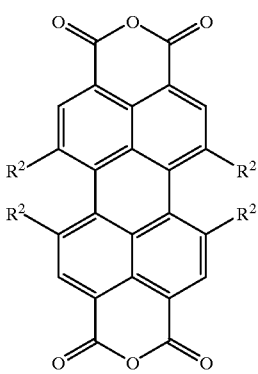

with an amide of the formula III

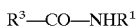

in which $R^3$ is hydrogen, $C_1$–$C_4$-alkyl or —$NR^4R^5$ where $R^4$ and $R^5$ independently are hydrogen or one of the $R^1$ alkyls, cycloalkyls, phenyls or naphthyls and where if two or more of $R^1$, $R^4$ and $R^5$ are other than hydrogen they are identical in the presence of an inert diluent and a transition metal catalyst and under superatmospheric pressure.

The alkyls in formulae I, II and III may be either straight-chain or branched. Substituted aryl may generally carry up to 3, preferably 1 or 2, of the substituents mentioned.

Specific examples of suitable radicals $R^1$–$R^5$ (or substituents thereof) are:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl and octadecyl (isooctyl, isononyl, isodecyl and isotridecyl are trivial names originating from the alcohols obtained by oxo synthesis—cf. Ullmanns Encyklopadie der technischen Chemie, 4th Edition, Volume 7, pages 215–217 and Volume 11, pages 435 and 436);

methoxy, ethoxy, propoxy, isopropoxy, butoxy, isobutoxy, tert-butoxy, pentoxy, isopentoxy, neopentoxy, tert-pentoxy and hexoxy;

phenyl, 2-naphthyl, 2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5 and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-cyanophenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

In the novel process for preparing the perylene-3,4-dicarboximides I, the perylene-3,4,9,10-tetracarboxylic dianhydrides II (or the corresponding acids) are not as with customary imidations reacted with primary amines but with amides of the formula III as amine equivalents, which facilitate controlled direction of the reaction, including in particular extensive suppression of the disruptive side reaction forming the unwanted perylenetetracarboxylic diimides and also permit the preparation of the N-$C_1$–$C_4$-alkyl imides I and the unsubstituted imides I.

Suitable amides III are both the appropriate N-substituted or unsubstituted amides ($R^1$=H) of aliphatic $C_1$–$C_4$ carboxylic acids, especially formic acid and acetic acid (case a) and also urea ($R^1$=H) and the appropriate N-monosubstituted, N,N- and N,N'-disubstituted and N,N,N'-trisubstituted urea derivatives ($R^1 \neq H$; case b). Preferred amides III are those which are at least partly soluble in the diluent used, since such amides can advantageously be added to the reaction mixture as a solution during the reaction in a controlled (continuous or else discontinuous) manner.

The carboxamides IIIa are preferably used to prepare perylene-3,4-dicarboximides of the formula I in which $R^1$ is (especially unbranched) $C_1$–$C_4$-alkyl or in particular is hydrogen or aryl.

The urea derivatives IIIb, especially the disubstituted and in particular the monosubstituted derivatives, can be used with advantage for preparing all perylene-3,4-dicarboximides I, including those where $R^1$ comprises branched and/or higher alkyl, cycloalkyl and aryl.

Specific examples of particularly suitable amides III are formamide, acetamide, N-methyl-, N-ethyl-, N-n-propyl- and N-n-butyl-, N-phenyl-, N-o-tolyl- and N-p-tolylformamide and -acetamide, urea, N-methyl-, N-ethyl-, N-propyl-, N-butyl-, N-pentyl-, N-hexyl-, N-heptyl- and N-octylurea, N,N- and N,N'-dimethyl- and N,N- and N,N'-diethylurea, and N-cyclopentyl-, N-cyclohexyl-, N-cycloheptyl-, N-cyclooctyl-, N-phenyl-, N-o-tolyl-, N-p-tolyl- and N-2-naphthylurea.

When the carboxamides IIIa are used the molar ratio of perylene-3,4,9,10-tetracarboxylic dianhydride II to IIIa is generally from 0.5:1 to 1.2:1, preferably from 0.9:1 to 1.1:1.

When urea and its derivatives IIIb are used, the molar ratio of II to IIIb is generally from 0.9:1 to 2.5:1, in the case of mono- and trisubstituted ureas preferably from 0.9:1 to 1.1:1, and in the case of urea itself and of disubstituted ureas preferably from 1.8:1 to 2.2:1.

The novel reaction of the perylene-3,4,9,10-tetracarboxylic dianhydrides II (or the corresponding acids) with the amides III is carried out in the presence of an inert diluent and a transition metal catalyst and under superatmospheric pressure.

Suitable diluents for this reaction are preferably tertiary nitrogen bases, for example cyclic imides, such as N-methylpyrrolidone, tertiary aliphatic amines $NR_3$ whose alkyl radicals R have 4 to 8 carbons, such as trihexylamine, and, in particular, aromatic heterocycles, such as pyridine, quinaldine, isoquinoline and especially quinoline.

The amount of diluent is not critical per se and is usually from 2 to 12 kg, preferably from 4 to 8 kg, per kg of perylene-3,4,9,10-tetracarboxylic dianhydride II.

Suitable transition metal catalysts other than zinc and its salts are, in particular, copper and its inorganic and organic salts, which are preferably employed in anhydrous form.

Examples of preferred salts are copper (I) oxide, copper (II) oxide, copper (I) chloride, copper (II) chloride, copper (I) bromide, copper (II) bromide, copper (II) acetate, copper (II) acetylacetonate, basic copper (II) carbonate and copper (II) sulfate.

Mixtures of the catalysts mentioned can also be used, of course.

In general the amount of catalyst used is from 20 to 150% by weight, preferably from 25 to 60% by weight, based on the perylene-3,4,9,10-tetracarboxylic dianhydride II.

The novel preparation process is expediently carried out in a closed, stirred pressure vessel (autoclave) under autogenous pressure, ie. the pressure established automatically in the closed system. In this case, during the reaction and depending on the chosen reaction conditions (for example the temperature of in general 120 to 250° C., preferably 160 to 200° C.), it is possible for a pressure of up to 25 bar to become established. Preference, however, is given to pressures of up to 18 bar.

It is advisable to operate under an inert gas atmosphere (for example nitrogen).

The novel reaction is normally over in 2 to 30 h, especially 3 to 12 h.

In terms of procedure the novel process can be carried out by adding all of the amide III at once to the reaction mixture before the latter is heated to reaction temperature, or metering in the amide III (preferably continuously), dissolved in a portion of the diluent used, into the reaction mixture which has been heated to reaction temperature.

In the former case, an expedient procedure is as follows:

The apparatus is charged with perylene-3,4,9,10-tetracarboxylic dianhydride II, catalyst and amide III in the entire quantity of diluent and the pressure apparatus is flushed with nitrogen (for about 15 minutes). After the apparatus has been closed, the mixture is heated with stirring to reaction temperature where it is stirred for about 3 to 8 h.

After the mixture has been cooled to a temperature of normally 20 to 50° C. and the apparatus has been let down, the reaction mixture can be worked up in accordance with one of the following variants:

Generally, about 1 to 1.5 times the amount of alcohol, preferably methanol, is added to the reaction mixture and the precipitated crude product is filtered off. Unreacted perylene-3,4,9,10-tetracarboxylic dianhydride II can be removed subsequently by stirring the product for from 0.5 to 1 hour in from about 6 to 10 times the amount of hot, dilute inorganic base (eg. 10% strength by weight potassium carbonate solution or 5 to 10% strength by weight potassium hydroxide solution), filtering the mixture again and washing the product first of all with a hot aqueous base, until the run off is colorless, and then with water until the run off is neutral.

Generally, from about 1 to 1.5 times the amount of alkyl acetate, especially $C_1$–$C_4$-alkyl acetate and, in particular, ethyl acetate is added to the reaction mixture, and the precipitated product is filtered off and washed first with further alkyl acetate until the run off is colorless and then with water to free it from solvent.

In both variants, complete removal of the catalyst can be effected by subsequently boiling the filter cake in dilute inorganic acid (for example 10–15% strength by weight hydrochloric acid) for 0.5 to 1 h.

Subsequently, the imides I can be isolated as usual by filtering the cooled mixture, washing the product with water until the aqueous run off is neutral and salt-free, and drying the product. In the second of the possible preparation procedures mentioned earlier, perylene-3,4,9,10-tetracarboxylic dianhydride II and catalyst are initially introduced in only a portion of the diluent (for example about half) and then, as described above, the mixture is flushed with nitrogen, the apparatus is closed and the mixture is heated to reaction temperature, before metering in the amide III, dissolved in the rest of the diluent, at a constant volume flow rate over the course of about 4 to 8 h. Following an after-stirring time of about 0.5 to 8 h, the reaction mixture is cooled, normally to 20–50° C., and the apparatus is let down. Subsequent working up can be carried out in a manner described above.

In general the products I treated in this way are already of such high purity (>80%) that further purification is unnecessary.

However, if it is desired to increase the purity to >98%, then the perylene-3,4-dicarboximides I can be subjected further to the purification techniques described in the nonprior-published DE-A-195 01 737, by first heating them in N-methylpyrrolidone and then treating the resulting N-methylpyrrolidone adducts with a base (especially an aqueous alkali metal hydroxide) under hot conditions and in the presence of an organic diluent (especially an aliphatic alcohol such as isopropanol), and subjecting if desired the subsequently isolated products to an additional treatment with a dilute inorganic acid (especially hydrochloric acid).

The novel preparation process can be used to prepare both perylene-3,4-dicarboximides which are substituted in the perylene framework and those which are unsubstituted in high yields (generally >70%) and high purities in an advantageous, simple and economic manner. In particular, it is also possible readily to obtain the perylene-3,4-dicarboximides I which are substituted by lower alkyl ($C_1$–$C_4$-alkyl, especially methyl) or are unsubstituted on the imide nitrogen.

EXAMPLES

Preparation of perylene-3,4-dicarboximides of the formula Ia

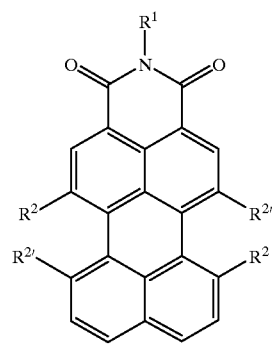

from perylene-3,4,9,10-tetracarboxylic dianhydrides of the formula IIa

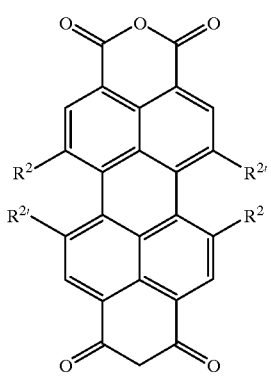

IIa

Examples 1 to 17

Process variant 1 (V1)

In a 1 l stirred pressure vessel, a mixture of 0.15 mol of the perylene-3,4,9,10-tetracarboxylic dianhydride IIa, 0.15 mol of the amide III (Example 1: 0.075 mol of urea; Examples 5 to 7: 0.075 mol of dimethylurea) and x g of the catalyst K in 300 ml of quinoline was flushed with nitrogen for 15 minutes. After the vessel had been given a pressure-tight seal, its contents were heated to T° C. with stirring and were maintained at this temperature for t h.

After cooling to room temperature and letting down of the reaction vessel, 400 ml of methanol were added to the reaction mixture. The crude product precipitated in this way was filtered off over a G3 glass frit and was washed with methanol until free from quinoline.

For further purification, the crude product was slurried in 500 ml of hot 10% strength by weight aqueous potassium carbonate solution, stirred at 80° C. for 1 h, filtered off again and washed first with hot potassium carbonate solution, until the run off was colorless, and then with water to neutrality. For complete removal of the catalyst, the filter cake was subsequently boiled in 500 ml of 10% strength by weight hydrochloric acid for 1 h, filtered off, washed with water until neutral and free from salt, and dried.

Process variant 2 (V2)

In a 1 l stirred pressure vessel, a mixture of 0.15 mol of the perylene-3,4,9,10-tetracarboxylic dianhydride IIa and x g of the catalyst K in 250 ml of quinoline was flushed with nitrogen for 15 minutes. After the vessel had been given a pressure-tight seal, its contents were heated with stirring to T° C. At this temperature, a solution of 0.15 mol of the amide III in 50 ml of quinoline (Example 8: +20 ml of N-methylpyrrolidone to increase the solubility) were metered in continuously via a pump over $t_1$ h.

Following an after-stirring time of $t_2$ h at T° C., the reaction mixture was cooled to room temperature, the apparatus was let down and the reaction mixture was worked up as described for process variant V1.

Further details of these experiments and their results, including the purities determined by quantitative thin-layer chromatography on silica gel against high-purity standards using a trichloroacetic acid/toluene mixture (1:3 to 1:10 v/v) as eluent, are compiled in the table below.

Note regarding Example 11:

The 1,7-diphenoxyperylene-3,4,9,10-tetracarboxylic dianhydride employed was obtained as described in the earlier German Patent Application 195 47 209.8 by brominating perylene-3,4,9,10-tetracarboxylic dianhydride, reacting the resulting 1,7-dibromoperylene-3,4,9,10-tetracarboxylic dianhydride with cyclohexylamine, reacting the N,N'-dicyclohexyl-1,7-dibromoperylene-3,4,9,10-tetracarboxylic diimide formed in the course of imidation, with phenol, and subsequently hydrolyzing the N,N'-dicyclohexyl-1,7-diphenoxyperylene-3,4,9,10-tetracarboxylic diimide.

TABELLE

| Ex. | $R^1$ | $R^2$ | $R^{2'}$ | Amide III | x g | K | V | T° C. | t h or $t_1$ h/$t_2$ h | Crude yield in % | Purity in % | Appearance | m.p. [° C.] |
|---|---|---|---|---|---|---|---|---|---|---|---|---|---|
| 1 | —H | —H | —H | urea | 20 | $Cu_2O$ | V1 | 180 | 4 | 70 | 80 | dark red, microcrystalline | >300 |
| 2 | —$CH_3$ | —H | —H | N-methyl-urea | 30 | $Cu_2O$ | V1 | 180 | 4 | 98 | 80 | dark red, microcrystalline | >300 |
| 3 | —$CH_3$ | —H | —H | N-methyl-urea | 60 | $Cu_2O$ | V1 | 180 | 4 | 95 | 80 | dark red, microcrystalline | >300 |
| 4 | —$CH_3$ | —H | —H | N-methyl-urea | 30 | CuCl | V1 | 180 | 4 | 95 | 80 | dark red, microcrystalline | >300 |
| 5 | —$CH_3$ | —H | —H | N,N'-di-methylurea | 15 | $Cu_2O$ | V1 | 180 | 4 | 95 | 90 | dark red, microcrystalline | >300 |
| 6 | —$CH_3$ | —H | —H | N,N'-di-methylurea | 30 | $Cu_2O$ | V1 | 180 | 4 | 98 | 85 | dark red, microcrystalline | >300 |
| 7 | —$CH_3$ | —H | —H | N,N-di-methylurea | 30 | $Cu_2O$ | V1 | 180 | 4 | 90 | 85 | dark red, microcrystalline | >300 |
| 8 | —$CH_3$ | —H | —H | N-methyl-urea | 30 | $Cu_2O$ | V2 | 180 | 4/0 | 95 | 85 | dark red, microcrystalline | >300 |
| 9 | —$C_4H_9$ | —H | —H | N-butyl-urea | 30 | $Cu_2O$ | V1 | 180 | 4 | 90 | 85 | dark red, microcrystalline | >300 |
| 10 | —$C_6H_{11}$ | —H | —H | N-cyclo-hexylurea | 30 | $Cu_2O$ | V1 | 180 | 6 | 80 | 85 | orange-red, microcrystalline | >300 |
| 11 | —$CH_3$ | —H | —OPh | N-methyl-urea | 30 | $Cu_2O$ | V1 | 170 | 6 | 85 | 85 | red-violet, microcrystalline | >300 |
| 12 | —$CH_3$ | —OPh | —OPh | N-methyl-urea | 30 | $Cu_2O$ | V1 | 180 | 6 | 90 | 85 | red-violet, microcrystalline | >300 |
| 13 | —H | —H | —H | formamide | 30 | $Cu_2O$ | V1 | 180 | 10 | 95 | 90 | dark red, microcrystalline | >300 |

TABELLE-continued

| Ex. | $R^1$ | $R^2$ | $R^{2'}$ | Amide III | x g | K | V | T° C. | t h or $t_1$ h/$t_2$ h | Crude yield in % | Purity in % | Appearance | m.p. [° C.] |
|---|---|---|---|---|---|---|---|---|---|---|---|---|---|
| 14 | —H | —H | —H | formamide | 30 | $Cu_2O$ | V1 | 200 | 6 | 98 | 90 | dark red, microcrystalline | >300 |
| 15 | —H | —H | —H | formamide | 30 | $Cu_2O$ | V2 | 190 | 8/4 | 90 | 90 | dark red, microcrystalline | >300 |
| 16 | —H | —H | —H | acetamide | 30 | $Cu_2O$ | V1 | 180 | 14 | 70 | 80 | dark red, microcrystalline | >300 |
| 17 | —Ph | —H | —H | acetanilide | 30 | $Cu_2O$ | V1 | 200 | 8 | 75 | 85 | brown-red, microcrystalline | >300 |

We claim:

1. A process for preparing perylene-3,4-dicarboximides of the formula I:

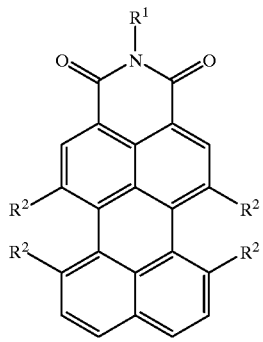

where $R^1$ is hydrogen; $C_1$–$C_8$-alkyl; $C_5$–$C_8$-cycloalkyl; or phenyl or naphthyl, each of which can be substituted by $C_1$–$C_{10}$alkyl, $C_1$–$C_6$-alkoxy or cyano; and $R^2$ independently at each occurrence is hydrogen;

$C_1$–$C_{18}$-alkyl; arylthio, 2-, 3- or 4-pyridyloxy, 2-, 3- or 4-pyridylthio, 2-, 4- or 5-pyrimidyloxy or 2-, 4- or 5-pyrimidylthio, each of which is optionally substituted by $C_1$–$C_{10}$-alkyl, $C_1$–$C_6$-alkoxy or cyano, which comprises reacting a perylene-3,4,9,10-tetracarboxylic acid or its anhydride of the formula II:

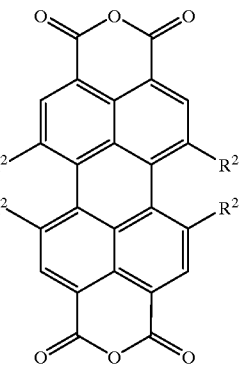

with an amide of the formula III:

$$R^3\text{—CO—NHR}^1 \qquad \text{III}$$

in which $R^3$ is hydrogen $C_1$–$C_4$-alkyl or —$NR^4R^5$ where $R^4$ and $R^5$ independently are hydrogen or one of the $R^1$ alkyls, cycloalkyls, phenyls or naphthyls and where if two or more of $R^1$, $R^4$ and $R^5$ are other than hydrogen they are identical, in the presence of an inert diluent and a transition metal catalyst or a zinc metal or salt catalyst and under superatmospheric pressure.

2. A process as claimed in claim 1, wherein the diluent used is a tertiary nitrogen-basic compound.

3. A process as claimed in claim 1, wherein the diluent used is quinoline, isoquinoline or quinaldine.

4. A process as claimed in claim 1, wherein the transition metal catalyst used is metallic copper or an inorganic or organic copper salt.

5. A process as claimed in claim 1, which is carried out under autogenous pressure.

6. A process as claimed in claim 1, which is carried out at from 120 to 250° C.

7. The process as claimed in claim 1, wherein said metal catalyst is metallic copper, metallic zinc or an inorganic or organic salt of copper or zinc or a mixture thereof.

* * * * *

UNITED STATES PATENT AND TRADEMARK OFFICE
CERTIFICATE OF CORRECTION

PATENT NO. : 6,136,976

DATED : October 24, 2000

INVENTOR(S): Arno Böhm, et al.

It is certified that an error appears in the above-identified patent and that said Letters Patent is hereby corrected as shown below:

On the title page, Item [75], the 1st Inventor's name is listed incorrectly. Item [75] should read as follows:

[75] Inventors: Arno Böhm, Mannheim; Harald Arms, Worms; Willi Helfer, Friedelsheim; Georg Henning, Ludwigshafen, all of Germany Signed and Sealed this Fifteenth Day of May, 2001

Attest:

NICHOLAS P. GODICI

Attesting Officer

Acting Director of the United States Patent and Trademark Office